United States Patent [19]
Johnson et al.

[11] Patent Number: 5,626,150
[45] Date of Patent: May 6, 1997

[54] EXTRICATION VACBOARD

[75] Inventors: David R. Johnson, Placitas; Mark B. Napier, Albuquerque, both of N.M.

[73] Assignee: University of New Mexico, Albuquerque, N.M.

[21] Appl. No.: 675,647

[22] Filed: Jul. 3, 1996

[51] Int. Cl.$^6$ ............................................. A61F 5/37
[52] U.S. Cl. ................................. 128/870; 5/628
[58] Field of Search ........................ 128/845, 846, 128/869–876; 602/5, 19; 5/628, 913

[56] References Cited

U.S. PATENT DOCUMENTS

| | | | |
|---|---|---|---|
| 4,234,982 | 11/1980 | Bez | 5/628 |
| 4,665,908 | 5/1987 | Calkin | 128/870 |
| 4,885,811 | 12/1989 | Hayes | 128/870 |
| 5,121,756 | 6/1992 | Koledin . | |
| 5,154,185 | 10/1992 | Latimer | 128/870 |

Primary Examiner—Michael A. Brown
Attorney, Agent, or Firm—Kenneth Callahan

[57] ABSTRACT

A combined long spine board and vacuum mattress device is disclosed that is designed to extricate, immobilize, and transport accident victims in emergency situations in which potential spinal injury is suspected. The superior extrication features of a rigid board are combined with the improved comfort and immobilization attributes of vacuum splint technology in a single device. Large wing vacuum mattresses that partially enclose the chest to knee region of a patient and small wings used to secure the patient's head are attached to the main vacuum mattress. Vacuum mattresses are airtight, flexible casings containing small beads and air. Evacuating these mattresses creates a semi-rigid bed conforming to the patient's body which immobilizes the patient in relative comfort. The large wings fold under the narrow main vacuum mattress/rigid board to present a narrow profile for extrication maneuvers. The full length rigid board facilitates extrication and transport.

7 Claims, 3 Drawing Sheets

EXTRICATION VACBOARD

BACKGROUND OF THE INVENTION

1. Field of the Invention

The present invention relates to backboards used in emergency extrication situations where possible spinal injuries may exist, and more particularly to a spinal immobilization device combining the superior extrication capabilities of a long spine board with the improved immobilization and comfort features of a vacuum splint.

2. Description of the Prior Art

The long spine board (LSB) has traditionally been used by emergency medical service (EMS) personnel as a platform to facilitate the extrication of accident victims from vehicles, to immobilize patients with suspected spinal trauma, and as a carrying device to transport the patient from the scene of the accident to the treatment facility. The LSB is a rigid board that is relatively narrow to permit access to automobile accident victims. In these situations, it is used to form a bridge between the seat of the automobile and the rescuers so that the patient can be positioned on it and then slid from the ear. The extrication of an accident victim, for example, might involve placing the LSB between the thigh of the injured person and the ear seat and subsequently sliding as much of the board as possible under the patient's body. Rescuers then use their hands to manually stabilize the head, neck, and back of the patient. A cervical collar may be employed at this point. The patient's hips are slowly rotated until the patient's body is parallel to the automobile seat. The patient's back is slowly lowered onto the LSB and the patient is then slid fully onto the LSB. In this position the patient is extricated from the ear and secured to the LSB with straps. Some type of head restraint is also used in conjunction with a cervical collar to immobilize the head. Thus immobilized, the patient is transported to an emergency department.

While the LSB is the most commonly used device for extrication, immobilization, and transportation of patients with spinal injuries, there are several problems. Patients immobilized on backboards frequently experience pain and discomfort from the board itself as well as from their injuries. It is often difficult for emergency staff to distinguish whether experienced pain is due to the immobilization or the injury, frequently resulting in unnecessary x-rays or other procedures. Furthermore, the degree of immobilization of a patient strapped to a rigid board is less than desirable. This can lead to additional spinal injury during the transportation process or while undergoing x-rays in an emergency room.

Various vacuum or air evacuated splint and mattress devices are known in the prior art, such as the vacuum immobilizer support of U.S. Pat. No. 5,121,756. A bag or casing is filled with small discrete elements such as round beads. A vacuum mattress or bag will conform to the patient's body when the patient is placed upon it. When the air is evacuated from the mattress, it becomes rigid while matching the contours of the patient's body, thus evenly supporting the body. When the patient is strapped to such a mattress, he is immobilized to a much greater degree than that which is possible using a rigid backboard. It is also much more comfortable for the patient. However, while the patient is sufficiently immobilized, the vacuum mattress is not sufficiently rigid by itself for extricating and transporting the patient. The patient is typically extricated to a backboard, then moved from the backboard to the vacuum splint. This additional handling could induce further injury and requires additional time.

While a LSB is a good extrication tool, it is a poor choice for immobilization of patients. Existing vacuum splints are good immobilization devices, but are too bulky and too flexible to be used as an extrication tool.

SUMMARY OF THE INVENTION

The present invention combines the best features of the rigid backboard and the vacuum mattress in a single device designed for the extrication, immobilization, and transportation of accident victims. This combination of a vacuum mattress and a rigid backboard has been labeled a "vacboard," hence the invention title, extrication vacboard.

In the preferred embodiment, the extrication vacboard consists of a rigid board approximately 72 inches long and 12 inches wide. The board fits within a sleeve. The main vacuum mattress is attached to the sleeve and extends from the top of the board to approximately 14 inches from the bottom of the board, such that an adult patient would be supported by the mattress from his head to just below the knees. A vacuum mattress is an air-tight casing that contains small beads which are compressed into a nearly rigid matrix when a vacuum is applied. A vacuum mattress is flexible and readily conforms to the patient's body contours prior to the application of a vacuum.

The extrication vacboard has two sets of "wings" that further support and immobilize the patient's body. Two large wings are attached to the main vacuum mattress, one on each side, to secure the patient to the device in conjunction with the strapping system. The wings are positioned between the patient's arms and torso and extend from under the patient's arms to the knee region. These wings are extensions of the main vacuum mattress being attached by partial seams which allow the passage of air but not the passage of the small beads. The partial seams also act as a hinge that permit the wings to pivot about the seam. The strapping system consists of three lateral straps attached to these wings that secure the legs, pelvis, and torso of the patient. Two additional straps form an "X" across the patient's chest; these straps are secured to the sleeve. The built-in strapping system is faster to apply than the traditional LSB strapping system and cannot be lost during the confusion of a rescue operation.

The patient's head is positioned on the main vacuum mattress between two small vacuum mattress wings located at the top end of the extrication vacboard. The small wings are attached to the main vacuum mattress by partial seams as are the large wings. The small wings enclose each side of the patient's head. The head is further secured by tape across the patient's forehead, the tape being attached to two webbing loops located on the underside of the device.

Three sets of handles are located along the longitudinal axis of the extrication vacboard for lifting. A first handle set is located between the large wings and the small wings and attached to the base of the sleeve. A second set is attached to the large wings themselves. The third handle set is located below the large wings and attached to the sleeve. Since the extrication vacboard does not rely on the vacuum mattress for its support, the vacuum mattress can be thinner and less bulky than existing vacuum splints.

The extrication vacboard is prepared for an extrication by folding the wings under the unit and securing them with a quick release strap. This reduces the profile of the device to around 12 inches facilitating its use in automobile extrication where space is limited. During an extrication, the device may be slid beneath the legs of the patient and the patient pivoted onto the vacboard. The vacuum mattress ends above the bottom of the board to reduce the thickness of the device so it may more readily be slid beneath the patient. Once the patient is positioned on the device, the main wings are brought around the patient and the patient is moved safely away from the accident scene.

The patient is then immobilized by securing the straps, positioning the small wings to secure the patient's head, and pulling a vacuum in the mattress/wing components. The patient's arms are secured by straps attached to the underside of the large wings. These straps hold the arms in a safe position, allow access for intravenous fluid delivery or measuring vital signs, and facilitate x-ray procedures once the person has been transported to the emergency department.

A significant advantage of the extrication vacboard is that the device does not interfere with access to the patient, allowing the device to be left in place while the patient is in the emergency department. The large wings can also be rotated away from the torso for a more thorough examination, even though they remain rigid under vacuum. The vacuum bed of the device increases the comfort of the patient, insulates the patient from the cold, and allows the device to be left in place longer, allowing more time to carefully examine the spine of the patient to determine the presence or absence of injuries. With traditional wooden or plastic spine boards, the discomfort of the patient due to the immobilization device itself often influences when the device is removed. The patient may be x-rayed in various positions while immobilized on the extrication vacboard.

The extrication vacboard is ideally suited for the extrication, immobilization, and transportation of accident victims with potential spinal injuries. It is also well suited for the transportation of any patient where spinal immobilization is required.

Other aspects and advantages of the extrication vacboard will become apparent from the following more detailed description taken in conjunction with the accompanying drawings.

DESCRIPTION OF THE PREFERRED EMBODIMENT

Figure 1:
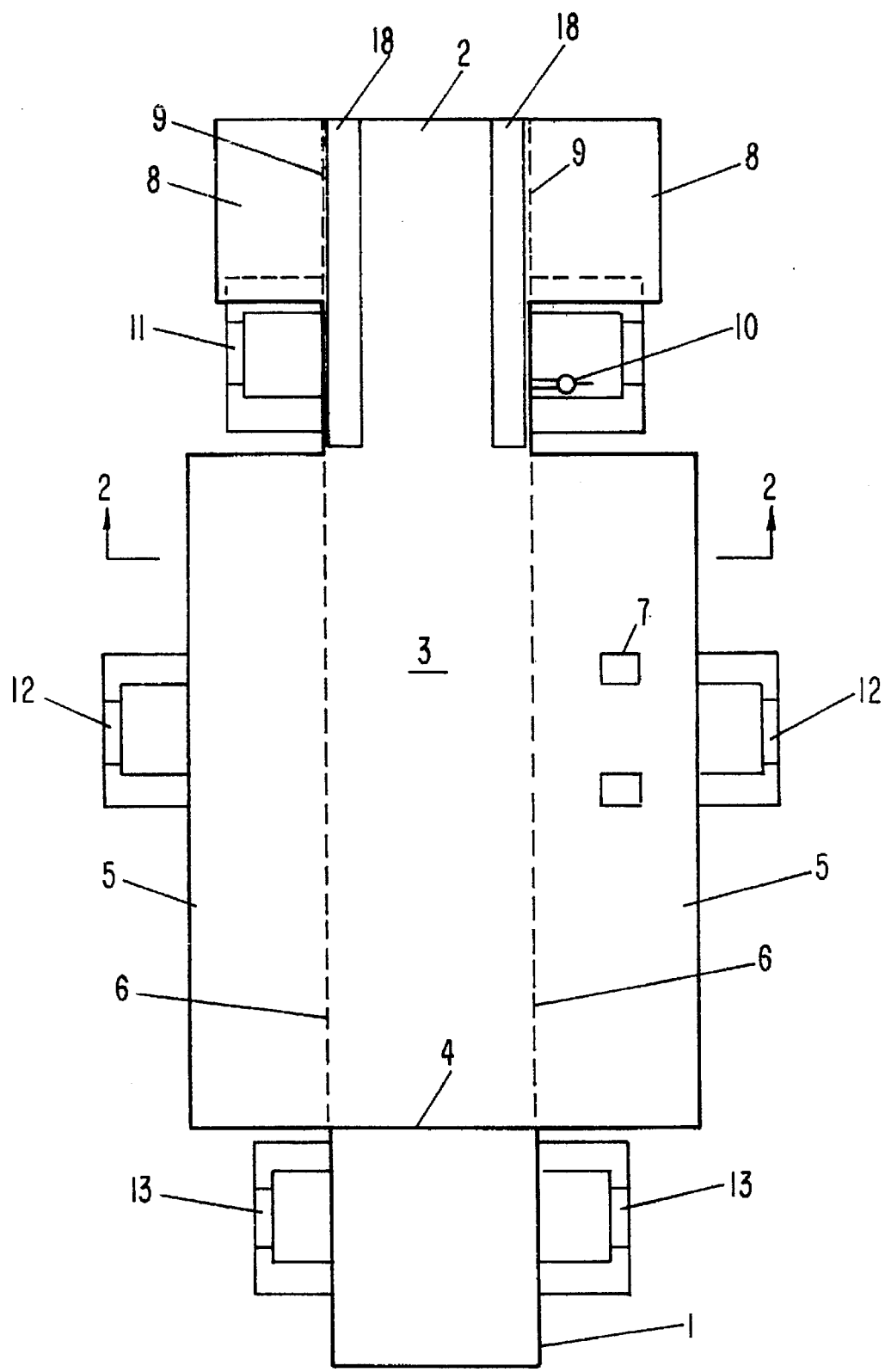
FIG. 1 is a front plan view of the extrication vacboard.

Referring to FIG. 1 of the front side of the extrication vacboard, the rigid board and sleeve 1 is approximately 12 inches wide and 72 inches long. The rigid board may be a 14-ply wood board, plastic, or any other suitable lightweight rigid material. The sleeve containing the rigid board serves as the anchoring point for the strapping system, handles, and main vacuum mattress. Secured to the front side of the sleeve starting at the head end 2 is the main vacuum mattress 3, an air-tight casing containing movable small beads or other discrete elements. The vacuum mattress is flexible when air is in the bag and conforms to the contours of a patient's body. When a vacuum is applied, however, it forms a semi-rigid matrix that follows the profile of the patient's body, thereby supporting the patient in a way that eliminates pressure points and uniformly distributes his or her weight. A patient lying on the main vacuum mattress/ rigid board would define certain regions of the extrication vacboard that will hereafter be referred to, i.e., the head, neck, torso (chest and pelvic regions), thighs, lower legs, and foot regions.

The attached main vacuum mattress it does not extend to the full length of the rigid board. It ends about 14 inches from the bottom or foot end at the full seam 4, leaving a relatively thin, narrow platform at the foot end to facilitate the extrication maneuvers.

Figure 2:
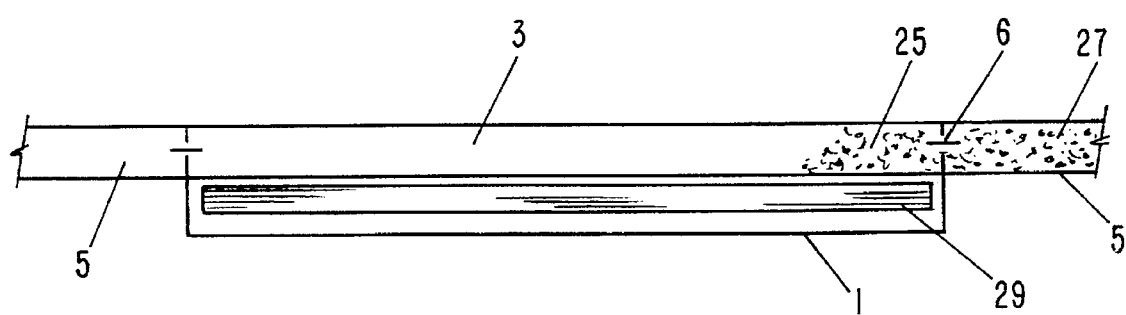
FIG. 2 is a cross-section of the extrication vacboard along the line 2—2 of FIG. 1.

Attached to the main vacuum mattress 3 are the two large wings 5, each having dimensions of about 8 inches in width and about 39 inches in length and extending from the approximate position of the underarms to the knees of an adult patient lying on the vacboard. The large wings are attached to the main mattress by partial seams 6 that provide a flexing point for the wings while permitting the passage of air but not the passage of the beads. These wings fold under the extrication vacboard when not in use, fastened with hook and loop material 7 or other securing means with a quick release. This provides the necessary narrow profile for extrication maneuvers. A cross-section of the vacboard is shown in FIG. 2, showing the rigid board 29, sleeve 1, main vacuum mattress 3, small, movable beads 25 in the main mattress, the large wings 5, the small, movable beads 27 within the large wing and the partial seams 6 connecting the wings to the main vacuum mattress.

Two small wings 8 are also attached by partial seams 9 to the main vacuum mattress 3 at the head end or top of the vacboard to secure the patient's head. There are two loops (21 of FIG. 3) attached to the sleeve on the underside of the small wings 8. The patient's head is secured to the vacboard using the small wings and adhesive tape extending across the patient's forehead and attached to these loops. The small wings 8 provide a built-in head immobilizer so that no extra device is needed as is required when a traditional LSB is used. The wings are themselves vacuum mattresses that become semi-rigid at the same time as the main vacuum mattress when evacuated. A battery-operated portable vacuum pump may be used to evacuate the vacuum mattresses via a single valve 10. The large wings may be made of padding and stiffening slats, but the vacuum mattress described is preferred.

Three pairs of handles are located along the longitudinal axis for carrying. A first handle set 11 is located in the neck region between the small and large wings and attached to the sleeve. The second pair of handles 12 are attached to the outer seams of the large wings at the pelvic region. The third pair of handles 13 are located below the large wings and attached to the sleeve.

The patient's torso is secured using five principal straps consisting of three straps attached to the sleeve and extending perpendicular to the longitudinal axis of the extrication vacboard. These three straps are located approximately at the top, middle, and bottom of the large wings (14, 15, and 16 of FIG. 3). Two additional diagonal straps are used to secure the chest in a cross-wise fashion. The lower portion of each of these straps (17 of FIG. 3) is attached to the sleeve on the underside of the large wings while the upper portion of each strap is attached to the top side of the sleeve above the large wings (18 in FIG. 1) and is stored with hoop and loop material. The top portion of these two straps is pulled down and across the patient's chest and connected to the corresponding lower portion.

Figure 3:
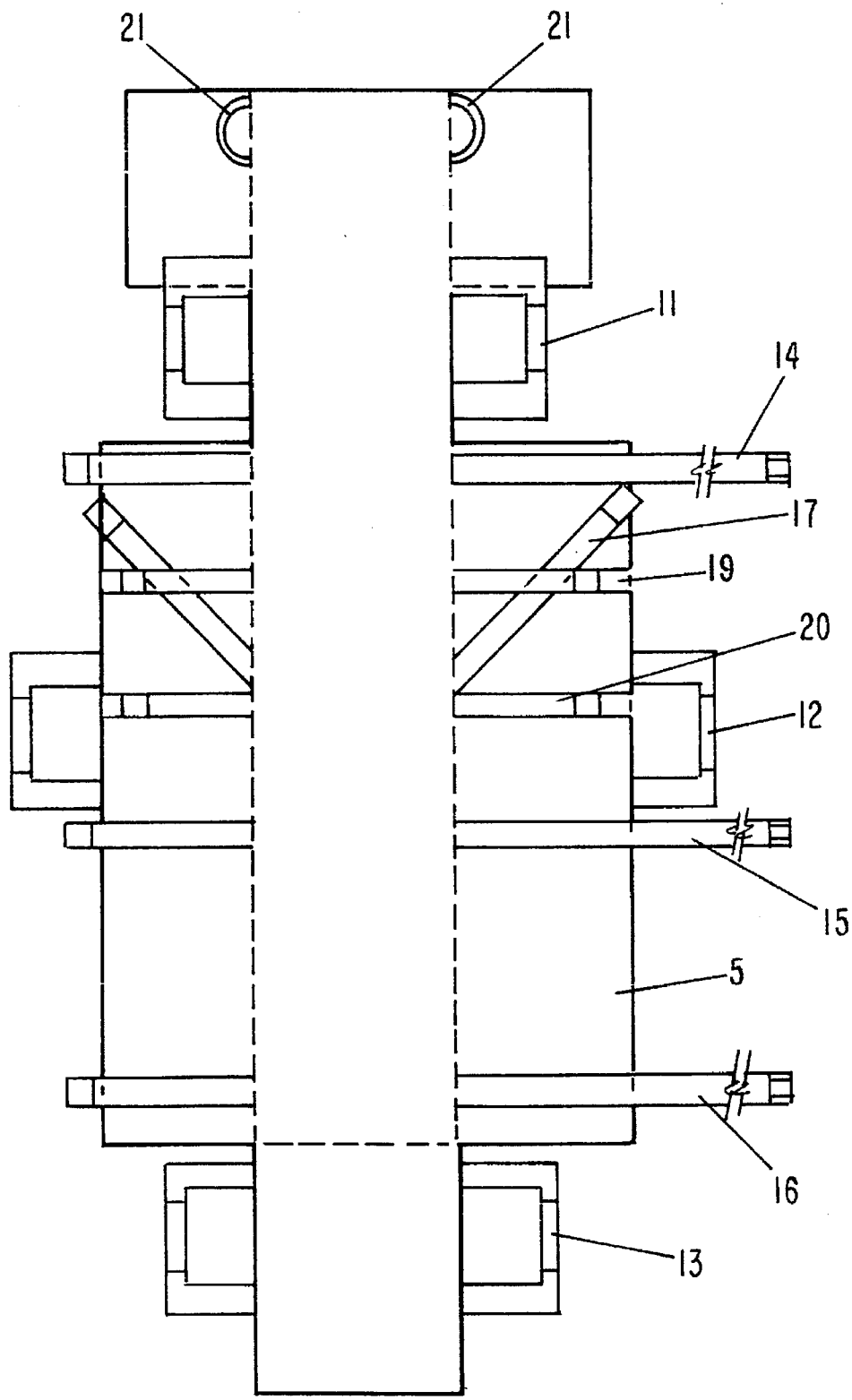
FIG. 3 is a back plan view of the extrication vacboard of FIG. 1.

The bottom side of each large wing also has two straps for securing the arms of the patient (19, 20 of FIG. 3). Securing the patient's arms outside of the primary spinal immobilization device allows access for intravenous fluid delivery, measuring vital signs, or facilitating x-ray procedures once the patient has been transported to the emergency department.

All straps are retained in position with elastic straps prior to use. The built-in strap system is faster to apply than the strapping system of a LSB and cannot be lost during the confusion of a rescue operation. The use of color coded straps allow rescuers to become proficient with the device with a minimum of training.

The design of the strapping system and the wings allows the extrication vacboard to accommodate a wide variety of body sizes and shapes. For small adults and children, the wings can be folded back away from them to allow access to the torso for treatment and monitoring. In larger adults, the full width of the wings can be used and the strapping system will firmly hold the body in place even if the wings do not surround the patient to the optimal degree.

The extrication vacboard has the flexibility needed for emergency situations. The design of the main wings allows a person to be safely carded in the device without the application of the full strapping system. In situations where speed is essential, a person can simply be rotated onto the device, the wings brought around them including their arms, and the whole system picked up and removed from the accident scene. This is advantageous when the safety of the rescuers and the patient is an issue. If the three horizontal straps are used alone, a high degree of immobilization can be obtained for temporary movement of the patient. The device, due to the central support member, can be used without applying the vacuum right away. The vacuum can be applied in the ambulance, or when time permits. The pre-hospital environment is highly fluid and the devices used to care for patients must be adaptable.

Traditional, full body vacuum splints cannot be picked up from the ends of the device. They are too flexible to maintain their shape during this type of maneuver. The extrication vacboard can be picked up from the ends due to the full-length support. Furthermore, since the extrication vacboard does not rely on the vacuum bed for its support, the volume can be less than existing vacuum splints, thereby reducing the bulk of the device. The extrication vacboard combines the extrication advantages of the LSB with the comfort and immobilization abilities of existing, full-length vacuum splints.

The present invention is, of course, in no way restricted to the specific disclosure of the specification and drawings, but also encompasses any modifications within the scope of the appended claims.

We claim:

1. An extrication vacboard device for the extrication, immobilization, and transport of patients comprising:

a) an elongated sleeve containing a rigid board having a head end, a foot end, a top side and a bottom side;

b) a main vacuum mattress upon which a patient can be placed comprising an airtight and flexible casing containing small beads and air attached to the top side of said elongated sleeve and being approximately the same width as said sleeve;

c) a large wing vacuum mattress attached to each elongated side of said main vacuum mattress by a partial seam, each large wing vacuum mattress being located such that it approximately extends from the arm pit to the knee region of an adult patient lying upon said main vacuum mattress with his head at the head end, and further, said partial seam permitting air but not said small beads to pass through and permitting said wing to pivot about said seam;

d) means to secure and quickly release said large wing vacuum mattresses to the bottom side of said sleeve, whereby the narrow profile of the extrication vacboard is available for extrication but can subsequently be quickly released to enclose the patient;

e) a small wing vacuum mattress attached to each elongated side at the head end of said main vacuum mattress by a partial seam;

f) evacuation valve means enabling evacuation of air from said main, small wing, and large wing vacuum mattresses for developing a vacuum in said mattresses to thereby convert said mattresses from a relatively flexible state to a semi-rigid state;

g) a first strapping means coupled to said sleeve adapted to extend across the large wing vacuum mattresses for urging the sides of said large wing vacuum mattresses against the patient's torso to thereby cradle and support the patient;

h) a first pair of carrying handles located on opposite sides of the sleeve between the small wings and the large wings;

i) a second pair of carrying handles located on opposite sides of the sleeve near the mid region of the large wings;

j) a third pair of carrying handles located on opposite sides of the sleeve near the foot end; and k) a second strapping means coupled to said large wings such that the patient's arms may be secured thereto.

2. An extrication vacboard support according to claim 1 wherein said elongated sleeve has dimensions of approximately 72 inches in length and 12 inches in width.

3. An extrication vacboard support according to claim 2 wherein said main vacuum mattress extends from the head end to within about 14 inches of the bottom end.

4. An extrication vacboard support according to claim 3 wherein said large wing vacuum mattresses have dimensions of approximately 39 inches in length and 8 inches in width.

5. An extrication vacboard support according to claim 4 wherein said means to secure and quickly release said large wing vacuum mattresses to the bottom side of said sleeve are comprised of hook and loop material.

6. An extrication vacboard support according to claim 4 wherein said first strapping means is comprised of three lateral straps located at the patient's chest, pelvic, and knee regions and two crossed chest straps all holding the large wing mattresses against the patient's torso.

7. An extrication vacboard support according to claim 6 wherein said crossed chest straps are secured to said main vacuum mattress by hook and loop material prior to being pulled down and across the patient's chest.

* * * * *